United States Patent [19]

Dombrowski et al.

[11] Patent Number: 5,151,518
[45] Date of Patent: Sep. 29, 1992

[54] N-ARYLATION OF ISATINS

[75] Inventors: James E. Dombrowski, Portland, Me.; Phillip G. Mattingly, Grayslake, Ill.

[73] Assignee: Abbott Laboratories, Abbott Park, Ill.

[21] Appl. No.: 443,869

[22] Filed: Nov. 30, 1989

Related U.S. Application Data

[63] Continuation of Ser. No. 271,799, Nov. 15, 1988, abandoned, which is a continuation-in-part of Ser. No. 104,715, Oct. 2, 1987, abandoned.

[51] Int. Cl.$^5$ .................. C07D 219/04; C07D 209/38
[52] U.S. Cl. ...................................... 546/107; 546/61; 546/102; 546/104; 548/451; 548/486
[58] Field of Search .................. 548/451, 486; 546/61, 546/102, 104, 107

[56] References Cited

PUBLICATIONS

*Organic Chemistry*, Fessenden, et al., Willard Grant Press, Boston, Mass. (1979) pp. 87, 91 and 162.
Albert, "The Acridines", 2nd ed., St. Martin's Press, New York, pp. 85-86, 558, 571, 578 (1966).
Barton, et al., *Tetrahedron Letters*, 27(31)3615-3618 (1986).
Barton, et al., *Tetrahedron*, 42(12):3111-3122 (1986).
Barton, et al., *Tetrahedron*, 43(2):323-332 (1987).
Barton, et al., *J. Am. Chem. Soc.*, 107:3607-3611 (1985).
Barton, et al., *Chem. Soc. Perkin Trans.*, I:241-249 (1987).
Barton, et al., *J. Chem. Soc. Perkin Trans.*, I:251-259 (1987).
Barton, et al., *Helvetica Chemica Acta*, 67:586-599 (1984).
Barton, et al., *J. Chem. Soc. Chem. Commun.*, pp. 65-66 (1986).
Barton, et al., *Tetrahedron*, 42(20):5627-5636 (1986).
Barton, et al., *Tetrahedron*, vol. 7, Supplement No. 1, pp. 73-79 (1981).
Barton et al., *J. Chem. Soc. Perkin Trans.*, 1:2657-2665 (1985).
Barton et al., *J. Chem. Soc. Perkin Trans.*, I:2667-2675 (1985).
Barton, et al., *J.C.S. Chem. Comm.*, pp. 1099-1100 (1978).
Barton, et al., *J.C.S. Chem. Comm.*, pp. 705-707 (1979).
Barton, et al., *J.C.S. Chem. Comm.*, pp. 246-247 (1980).
Barton, et al., *J.C.S. Chem. Comm.*, pp. 827-829 (1980).
Barton, et al., *J.C.S. Chem. Comm.*, pp. 503-504 (1981).
Barton, et al., *Tetrahedron Letters*, 27(31):3619-3622 (1986).
Barton, et al., *Tetrahedron Letters*, 29(10):1115-1118 (1988).
Coppola, *J. Heterocyclic Chem.*, 24(5):1249-1251 (1987).
David, *Tetrahedron Letters*, 22(50):5063-5066 (1981).
David, et al., *J. Org. Chem.*, 48:441-447 (1983).
Dodonov, et al., *Zhurnal Obshehei Khimii*, 55(1):63-68 (Jan. 1985).
Dodonov, et al., *Chemical Abstracts*, vol. 103, Abstract 22218z (1985).
Dodonov, et al., *Chemical Abstracts*, vol. 106 Abstract 5162w (1987).
Glidewell, *Journal of Organometallic Chemistry*, 106:199-209 (1976).
Goel, et al., *Canadian Journal of Chemistry*, 48:2488-2493 (1970).

*Primary Examiner*—Diana Rivers
*Attorney, Agent, or Firm*—Frank S. Ungemach; Priscilla F. Porembski; Daniel W. Collins

[57] ABSTRACT

A process for the N-arylation of isatins with organo bismuth reagents is disclosed.

8 Claims, No Drawings

N-ARYLATION OF ISATINS

This application is a continuation of application Ser. No. 271,799, filed Nov. 15, 1988, which is a continuation-in-part of application Ser. No. 104,715, filed Oct. 2, 1987, entitled "N-Arylatin of Isatins" both obtained.

BACKGROUND OF THE INVENTION

The present invention relates to a process and intermediates for the production of N arylated isatins which are in turn used in the manufacture of N alkyl acridine sulfonamide chemiluminescent labels.

As disclosed in copending U.S. patent application Ser. No. 921,979 entitled Chemiluminescent Acridinium Salts filed on Oct. 22, 1986 by Mattingly et al. (the disclosure of which is incorporated herein by reference), such salts are useful in chemiluminescent immunoassays (CLIAs). In CLIAs, an antibody (or antigen) is labeled with a chemiluminescent moiety, and the labeled antibody (or antigen) is introduced to a sample containing the corresponding antigen (or antibody) to be detected or measured. Once the labeled antibody (or antigen) binds to the corresponding antigen (or antibody), the presence or amount of antigen (or antibody) in the sample can be determined, depending upon the type of assay format utilized. There are various assay formats: enzyme immunoassays, radioimmunoassays, fluorescent polarization immunoassays, and the like. Chemiluminescent immunoassays may thus match or exceed the sensitivity of radioimmunoassays (RIA), or enzyme immunoassays (EIA). [Kircka et al., Diagnostic Medicine, 1, 45 52 (1984].

Substituted acridine 9 carboxylic acid compounds have been demonstrated to be useful in CLIAs. To make such compounds, one can directly substitute an existing acridine compound. However, direct substitution often achieves low yields, forms many isomers, and often destroys other functional groups on the acridine rings. Substituted acridine 9 carboxylic acid compounds can also be prepared with the Jourdan Ullmann Goldberq synthesis and/or Chapman rearrangements. These procedures are labor intensive, unfortunately, and the substituted acridines formed from the cyclization of diphenyl amines often cannot be converted to the 9-carboxylic acids with known techniques. Finally, acridine 9 carboxylic acids can be prepared with a Pfitzinger rearrangement of isatins and ketones, with subsequent aromatization of the final ring on the acridine. But, low yields are often encountered, isomers are formed, and other functionalities on the acridine ring are often destroyed. This reaction scheme is also labor intensive and performed under harsh conditions. Accordingly, simple, economic processes for making acridines have been sought.

N-arylation of amines was disclosed by Barton et al "Metallic Copper Catalysts of N-Arylation of Amines," *Tetrahedron Letters*, Vol. 27, No. 31, pp. 3615-3618 (1986). However, amines are nucleophillic species, and are chemically reactive. By contrast, the amide (e.g. isatin) nitrogen is typically not considered nucleophillic. Presently, there is no good method of converting an unsubstituted isatin to the N-aryl isatin.

SUMMARY OF THE INVENTION

The present invention is a simple, economical process for making substituted acridine-9 carboxylic acids. Isatins are N-arylated with triaryl bismuth reagents and copper or copper salts. The substituted, N arylated isatins are subsequently rearranged to produce substituted acridines. This is a regiospecific (i.e. provides predominantly one regioisomer) process, which allows direct synthesis of isomerically pure substituted acridines in good yields. This process affords the production of acridines with different functional substitutions.

The process of the current invention involves the N-arylation of isatins by (a) reacting a compound of formula I wherein A, B, C and D are selected independently in each instance from hydrogen, halogen, cyano, nitro, amino, carboxy, sulfone, and alkoxy, or B and C together can form a fused aromatic ring:

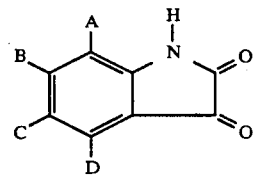

(b) with a compound of formula II:

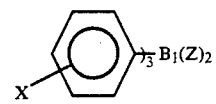

where X is selected from one or more of hydrogen, halogen, nitro, cyano, alkyl and alkoxy. Z is either a halogen or a substituent of formula III:

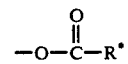

with the proviso that where Z is a halogen, a salt of the formula

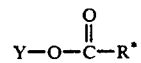

is added to the reaction mixture. Y is a group I or group II metal, and R* in each instance is selected from a group such that the conjugate acid of the group of formula III has a pka in water of less than 5.0. The reaction above is performed in the presence of a copper catalyst to produce an N-arylated isatin of formula IV:

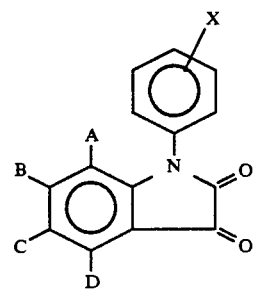

The N arylated isatin of formula IV is treated with a strong base, and heated to produce an acridine compound of formula V:

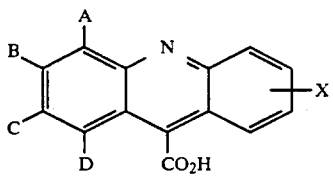

V

DETAILED DESCRIPTION

In this invention, as indicated above, an isatin of formula I is reacted with a triaryl bismuth reagent of formula II in the presence of copper or a copper salt to produce an N-arylated isatin of formula IV which can be converted to an acridine of formula V. The acridine can then be converted to a chemiluminescent label as described in U.S. patent application Ser. No. 921,979 filed Oct. 22, 1986 which is incorporated herein by reference.

As indicated above, the substituent $R^*$ in formula III is selected from a group such that the conjugate acid of the group of formula III have a pKa in water of less than 5.0. By "conjugate acid of the group of formula III" is meant an acid of the formula:

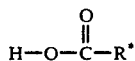

Preferred substituents for $R^*$ include hydrogen, cyano, alkyl, halo substituted alkyl or cyano substituted alkyl. The most preferred substituents for $R^*$ include trifluoromethyl or methyl.

Further details of the foregoing scheme are described in examples that follow. In these examples, two general approaches are described. First, the bismuth arylating reagent can be presynthesized as described in Example 1. Alternatively, the bismuth arylating reagent can be generated in situ (i.e. during the arylation of the isatin) as illustrated in the following reaction scheme and in Example 3(b).

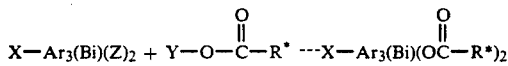

where Y is a group I or group II metal), Z is a halogen, is an aryl, and X is as defined above.

The following examples illustrate the preparation of N-arylated isatins and acridines. The conversion of acridines to chemiluminescent compounds is described in the foregoing U.S. patent application.

Reference to symbols such as X, A, B, C and the like in the following examples correspond to the meanings those symbols have been given above.

EXAMPLE 1

Synthesis of Triphenyl Bismuth Diacetate

Silver acetate (5.12 grams) and water (1 1) were placed in a 3 1 round bottom flask, kept under a nitrogen atmosphere, and the flask was covered with foil. To this suspension were added triphenyl bismuth dichloride ($Ph_3BiCl_2$ Alfa Products, Danvers, MA; 7.06 grams) and benzene (800 ml). The mixture was stirred mechanically in the dark for two days.

The mixture was then suction filtered, and the residue was rinsed with benzene (50 ml). The white, insoluble residue (which discolors to a violet tint) was discarded.

The two phase filtrate was then placed in a separatory funnel. The two layers were then separated, and the aqueous layer discarded. The benzene layer was then evaporated to a volume of 200 ml. Petroleum ether (700 ml) was added. A white precipitate forms and was collected by suction filtration. The filtrate was dried overnight under a vacuum, yielding 4.91 g of triphenyl bismuth diacetate (X=H). NMR 1.80 (6H,s); 7.67 (9H,m); 8.19 (6H,m); Ms m/z @499 (M—$OCOCH_3$).

EXAMPLE 2

Synthesis of N-phenyl Isatin

Isatin (25 mg from Aldrich, Milwaukee, Wisconsin) was placed in a 25 ml round bottom flask under a nitrogen atmosphere. Triphenyl bismuth diacetate (300 mq) from Example 1 and freshly distilled methylene chloride (from $P_2O_5$; 10 ml) was then added, maintaining the nitrogen atmosphere. Copper powder (3 mg) was then added. The reaction mixture was then stirred at reflux for four hours. An additional portion of triphenyl bismuth diacetate (95 mg) was added, and the mixture was refluxed for twelve hours more. The desired product, N-phenyl isatin (42.1 mg) was obtained and purified on a 2 mm silica prep plate (ANALTECH UNIPLATE Silica Gel GF. 1:1 hexane/ethyl acetate).

Melting point: 138°–139.5° C.,

NMR: δ6.90 (1H,d), 7.17 (1H,t), 7.50 (6H,m), 7.69 (1H,d) ppm ,

MS: (M+)@223

EXAMPLE 3

Synthesis of N phenyl 5 nitroisatin a) 5-Nitroisatin (53 mg; Aldrich N 1780 7), triphenyl bismuth diacetate (304 mg), and freshly distilled methylene chloride (about 10 ml) were placed in a 25 ml flask under a nitrogen atmosphere. To this dull yellow suspension, copper powder (5 mg) was added. For seven hours, the mixture was then heated to reflux by placing it in an oil bath while stirring the mixture. Additional triphenyl bismuth diacetate (95 mg) was added and allowed to stir at reflux overnight. The mixture was evaporated to dryness and purified on a 2mm silica plate as in example 2. An orange residue (56.3 mg) was obtained.

(A=H, B=H, C=NO2, D=H, X=H),

NMR: δ7.15 (1H,d), 7.52 (5H,m), 8.46 (1H,d), 8.55 (1H,s) ppm

MS: (M+)@268 b) Alternatively, N-phenyl 5 nitroisatin was prepared by the in-situ bismuth arylating reagent generation scheme outlined above. 5-nitroisatin (100.3 mg), triphenyl bismuth dichloride (400 mg), copper powder (10 mg), and methylene chloride (40 ml) were placed in a 50 ml flask. The mixture was heated to reflux under a nitrogen atmosphere while stirring. After three hours, no reaction was observed although bismuth reagent decomposition was noted whereupon additional triphenyl bismuth dichloride (220 mg) was added. The mixture was stirred and refluxed overnight after which arylation was still not observed.

Then, sodium acetate (300 mg) and triphenyl bismuth dichloride (200 mg) were added together to the mixture. The mixture was refluxed overnight, and more sodium acetate (150 mg) and triphenyl bismuth dichloride (200 mg) were added. The reaction mixture was cooled to room temperature and filtered. The filtrate was evaporated to dryness. The orange residue produced was purified on 3×2 mm silica prep plates (as in example 2). Analysis of the residue (48 mg) confirmed that the title compound was prepared.
(A=H, B=H, C=NO2, D=H, X=H).
NMR: δ7.15 (1H,d), 7.52 (5H,m), 8.46 (1H,d), 8.55 (1H,s) ppm
MS: (M+)@268

EXAMPLE 4

Synthesis of N phenyl benz[f]isatin

Linear benz[f]isatin (Eteine, A.; Staehelin, A.; *Bull. Chim. Soc. Fr.*, 1954, 243–748) (50 mg), triphenyl bismuth diacetate (354 mg), and methylene chloride (about 15 ml) were placed into a 25 ml flask under a nitrogen atmosphere. To this bright orange mixture was added copper powder (4.5 mg). The mixture was then heated to reflux while stirring for 12 hours.

Additional triphenyl bismuth diacetate (50 mg) and methylene chloride (3 ml) were added, and the mixture was refluxed for 48 hours. The mixture was dried, and purified on a 2 mm silica plate (4:6 ethyl acetate/hexanes). A red solid (20.5 mg) was obtained.
(A=H, B&C=fused phenyl; D=H, X=H)
NMR: δ7.05 (1H,s); 7.52 (8H,m); 7.94 (1H,d); 8.27 (1H,s) ppm.
MS: (m +H)@274:

EXAMPLE 5

Synthesis of N phenyl 5 bromoisatin

5 Bromoisatin (55 mg; Aldrich No. 12, 407-9), triphenyl bismuth diacetate (340 mq) and methylene chloride (about 15 ml) were placed in a 25 ml flask under a nitrogen atmosphere. To this yellow solution was added copper powder (4.5 mg). The mixture was then heated to reflux in an oil bath while stirring for 24 hours. Additional triphenyl bismuth diacetate (90 mg), and methylene chloride (3 ml) were added, and the mixture was refluxed for 12 hours. Finally, additional (triphenyl bismuth diacetate; 59 mg) and methylene chloride (3 ml) were added, and the mixture refluxed for two more days.

The mixture was suction filtered through Celite®, and rinsed with ethylacetate. The reddish yellow residue was dried, and purified on a 2 mm silica plate (4:6 ethylacetate/hexanes). The purified residue weighed 26.8 mg.
(A=H, B=D=X=H, C=Br)
NMR: δ6.72 (1H,d); 7.52 (6H,m); 7.80 (1H,s)
MS: (M+)@301, 303

EXAMPLE 6

Synthesis of N phenyl 5-methylisatin

5-Methylisatin (53 mg; Aldrich No. 22, 242-9), triphenyl bismuth diacetate (278 mg), copper powder 5 mg), and methylene chloride (about 15 ml) were placed in a 25 ml flask under a nitrogen atmosphere. The orange solution was then heated to reflux in an oil bath for fourteen hours. Then, additional triphenyl bismuth diacetate (154 mq) was added, and the mixture was refluxed for eight hours. Additional triphenyl bismuth diacetate (158 mg) was added, and the mixture was refluxed for about twelve hours. The heat was then removed, and the mixture was stirred for two days.

The mixture was suction filtered through Celite-® and evaporated to dryness. The mixture was purified on 32 mm silica plates (4:6 ethylacetate/hexanes) and 57.3 mg of the title compound was obtained.
(A=H, B=D=X=H, C=CH3)
NMR: δ2.30 (3H,s); 7 52 (1H,d); 7.19 (8H,m)
MS: (m+H)@238

EXAMPLE 7

Synthesis of N phenyl 5 cyanoisatin 5-cyanoisatin [prepared by the method of Gassman, et. al., *J. Org. Chem.*, 42, 1344 (1977)](50 mg, 0.29 mmoles), triphenyl bismuth diacetate (300 mq) and copper powder (3 mg) were added to 10 mL of methylene chloride (freshly distilled). The reaction mixture was heated to reflux under nitrogen for a total of 16 hours during which additional triphenyl bismuth diacetate (95 mg) was added at four hour intervals. The product was isolated after evaporating the reaction mixture to dryness then purifying by preparative TLC as in example 2.
(A=H, B=H, C=CN, D=H, X=H)

EXAMPLE 8

Synthesis of N phenyl 5 carboxy methyl isatin 5-carboxy methyl isatin [Bauer, et al., *Brit J. Pharmacol*, 15, 101 (1960)](50 mg, 0.24 mmoles), triphenyl bismuth diacetate (300 mg) and copper powder (3 mq) were added to methylene chloride (10 mL). The reaction mixture was refluxed under nitrogen for 16 hours during which time additional triphenyl bismuth diacetate (95 mg) was added at four hour intervals.

N-phenyl 5 carboxy methyl isatin was isolated after evaporation of the reaction mixture and purification by preparative TLC as in example 2.
(A=H, C=CH2CO2H, B=H, X=H)

EXAMPLE 9

Synthesis of N phenyl 5 amino isatin 5 amino isatin [Ger. Offen. 2,144,877] was treated with di-t butyl dicarbonate [Aldrich, #20,524 9] in tetrahydrofuran water (1:1) in the presence of an equivalent amount of triethyl amine. After stirring overnight at room temperature, the reaction mixture was diluted with ethyl acetate and washed with dilute hydrochloric acid, brine and dried over MgSO4. 5 (N-'Boc-amino)isatin was isolated on evaporation.

This material (50 mg, 0.19 mmoles), triphenyl bismuth diacetate (300 mg) and copper powder (3 mg) was heated to reflux in 10 mL of methylene chloride under nitrogen for 16 hours, with the addition of more triphenyl bismuth diacetate at four hour intervals.

The N-phenyl-5-(N-'BOC-amino)isatin was isolated as in example 2, then treated with trifluoroacetic acid in methylene chloride at 0° C for 30 minutes under nitrogen. N-phenyl-5-amino isatin was isolated on evaporation of the reaction mixture.
(A=H, C=NH2, B=H, X=H)

EXAMPLE 10

Synthesis of N phenyl-5-methoxy isatin 5 methoxy isatin [Bachman, et al., *J. Amer. Chem. Soc.*, 1599 (1946)]. (50 mg, 0.28 mmoles), triphenyl-bismuth diacetate (300 mg) and copper powder (3 mg) were heated to reflux in methylene chloride (10 mL) under nitrogen for 12 hours with the addition of more triphenyl bismuth diacetate (95 mg) at four hour intervals.

N-phenyl 5-methoxy isatin was isolated as in example 2.

(A=H, C=OCH₃, B=H, X=H)

EXAMPLE 11

Synthesis of N phenyl-isatin 5 sulfonic acid

Isatin 5-sulfonic acid (Aldrich, #14,933-0) (50 mg, 0.2 mmoles), triphenyl bismuth diacetate (300 mg) and copper powder (3 mg) were heated to reflux in methylene chloride (10 mL) under nitrogen for 24 hours with addition of additional amounts of triphenyl bismuth diacetate (4×95 mg) over that time.

N phenyl isatin 5 sulfonic acid was isolated after evaporation of the reaction mixture, and purified on C-18 reversed phase preparative TLC plates [2, 1mm Whatman PLKC18F].

(A=H, B=H, C=SO₃H, X=H)

EXAMPLE 12

Synthesis of N-phenyl 7 methyl isatin 7-methyl isatin [Gassman et al., *J. Org. Chem.*, 42, 1344 (1977)] was treated with triphenyl bismuth diacetate and copper powder as in example 6 to yield N phenyl 7 methyl isatin.

(A=CH₃, B=H, C=H, X=H)

EXAMPLE 13

Synthesis of N phenyl 6-methyl isatin 6-methyl isatin [Grimshaw, et al., *Synthesis*, 496 (1974)] was treated with triphenyl bismuth dracetate and copper powder as in example 6 to yield N phenyl-6-methyl isatin.

(A=H, B=CH₃, C=H, X=H)

EXAMPLE 14

Synthesis of N phenyl 5-(2 aminoethyl)isatin 4-nitrophenethyl amine hydrochloride [Aldrich #18,480-2] was treated with di-t-butyl dicarbonate in tetrahydrofuran with excess triethyl amine to form N-$^t$Boc (4 nitrophenethyl)amine. Reduction with 5% pd/c in methanol (50 psi H₂) yielded N-$^t$Boc-(4 aminophenethyl)amine. Treatment with oxalyl chloride and cyclization gives the isatin [Baumgarten, et. al, *J. Org. Chem.*, 1961, 26, 1536]. This material was treated with triphenyl bismuth diacetate as in example 8, to yield N phenyl 5-(N-t-Boc 2 amino ethyl) isatin. The t-Boc protecting group was removed as in example 8 to give N-phenyl 5 (2-aminoethyl)-isatin.

(A=H, B=H, C=CH₂CH₂NH₂, X=H)

EXAMPLE 15

Synthesis of N (4-methoxy phenyl)isatin

Tri-(4 methoxy phenyl)bismuth dichloride [Barton, et al., *Tetrahedron*, 42, 3111 (1986)] was converted to this diacetate following the procedure in example 1. Using this material, isatin was converted to N-(4-methoxy phenyl)isatin as in example 2.

(A=H, B=H, C=H, X=OCH₃)

EXAMPLE 16

Synthesis of N-(4 nitrophenyl)isatin

Tri (4-nitrophenyl)bismuth dichloride [Barton, et al., *Tetrahedron*, 42, 3111 (1986)] was converted to this diacetate as in example 1. The arylation of isatin as in example 2 led to N-(4-nitrophenyl)isatin.

(A=H, B=H, C=H, X=4 NO₂)

EXAMPLE 17

Synthesis of N-(3-nitrophenyl)isatin

Tri-(3-nitrophenyl)bismuth dichloride [Ptitsyna, et al., *Chem. Abst.*, 57, 15147 (1962)] was converted to the diacetate as in example 1. The arylation of isatin as in example 2 led to N-(3 nitrophenyl)isatin.

(A=B=C=H, X=3 NO₂)

EXAMPLE 18

Synthesis of N-(o-tolyl)isatin o-Tolyl magnesium bromide (Aldrich 29, 898 0) was converted to tri-(o tolyl)bismuth dichloride on reaction with bismuth trichloride (Aldrich #22, 483 9) following the procedure outlined in Barton, et al., *Tetrahedron*, 42, 3111 (1986). The diacetate was formed as in example 1. The arylations of isatin as in example 2 led to N-(o tolyl)isatin.

(A=B=C∇H, X=2 CH₃)

EXAMPLE 19

Synthesis of Benz[b]acridine 12 carboxylic acid

The title compound can be prepared by placing N phenyl-benz [f]isatin (16 mg) from Example 4 and 10% KOH solution (10 ml) into a 35 ml flask. The bright orange solution is heated overnight on a steam bath in the dark.

The bright orange solution is removed from the steam bath and suction filtered to remove an orange brown precipitate of benz[b]acridin 12-one. The filtrate is acidified to pH 0 to 1 with concentrated hydrochloric acid. A purple precipitate is formed and collected by suction filtration.

(A=H, B&C=fused phenyl; D=X=H)

NMR: (CD₃OD/NaOD) 7.2-7.5 (4Hm); 7.8 (2H (2H,m); 8.83 (1H,s); 8.93 (1H,s),

MS: (m+64)@337 corresponding to the hydrate+2 Na

EXAMPLE 20

Synthesis of 2 bromo acridine 9 carboxylic acid

The title compound can be prepared by placing N phenyl-5 bromoisatin (20 mq) from Example 5 and 10% KOH solution (10 ml) in a 25 ml flask. The bright yellow mixture is heated in a steam bath overnight.

The solution is suction filtered, and the filtrate is acidified with concentrated hydrochloric acid to pH 0 to 1. A bright yellow precipitate forms, and is collected by suction filtration.

(A=B=H, C=Br, D=H, X=H)

NMR: (CD₃OD/NaOD) 7.66 (1H,m); 7.9 (2H,m); 8.22 (3H,m); 8.46 (1H,s)

MS: (m+)@301,303

EXAMPLE 21

Synthesis of 2 methyl acridine 9 carboxylate

The title compound can be prepared by placing N-phenyl-5 methyl isatin (40 mg) from Example 6 and 10% KOH solution (10 ml) in a 25 ml flask. The orange mixture is then heated overnight on a steam bath. The clear yellow solution is then filtered, and the filtrate is acidified to pH 0 to 1 with concentrated hydrochloric acid. A bright yellow precipitate forms and is collected by suction filtration.

(A=B=H, C=CH₃, D=X=H)

NMR: (CD$_3$OD/NaOD) δ2.54 (3H,s); 7.66 (3H,m); 8.08 (4H,m)
MS: (m+)@237

EXAMPLE 22

Synthesis of 2-nitro-acridine-9-carboxylic acid

The title compound can be prepared by placing N-phenyl 5 nitroisatin (40 mg) from Example 3 and 10% KOH solution (10 ml) into a 25 ml flask. The dark amber mixture is then heated overnight on a steam bath. The dark brown solution is then suction filtered to collect a black insoluble solid. The filtrate is acidified to pH 0 to 1 with concentrated hydrochloric acid. The dark brown filtrate is then filtered, and the golden brown filtrate is neutralized to pH 7-8 and evaporated to dryness.

The collected precipitate from acidification is placed under a high vacuum, and evaporated to dryness.

(A=B=D=X=H; C=NO$_2$)

EXAMPLE 23

Synthesis of 2 cyano acridine 9 carboxylic acid

The title compound can be prepared from N-phenyl 5 cyano isatin of example 7 and 10% KOH by heating for 12 h on a steam bath. The solution is filtered, then acidified to pH 1 with concentrated sulfuric acid and the product collected by filtration.

(A=B=H, C=CN, X=H)

EXAMPLE 24

Synthesis of 2 carboxymethyl acridine 9 carboxylic acid

The title compound can be prepared from N phenyl-5 carboxy methyl isatin of example 8 and 10% KOH by heating for 12 h on a steambath. The solution is filtered, then acidified to pH 1 with conc. sulfuric acid, and the product is collected by filtration.

(A=B=H, C=CH$_2$COOH, X=H)

EXAMPLE 25

Synthesis of 2 amino-acridine 9 carboxylic acid

The title compound can be prepared from N-phenyl-5 amino isatin of example 9 and 10% KOH by heating for 12 hours on a steam bath. The solution is filtered, then acidified with conc. sulfuric acid. The product is collected by filtration.

(A=B=H, C=NH$_2$, X=H),

EXAMPLE 26

Synthesis of 2-methoxy acridine 9 carboxyl acid

The title compound can be prepared from N-phenyl-5-methoxy isatin of example 10 and 10% KOH by heating 2 hours on a steam bath. The solution is filtered, then acidified to pH 1 with conc. sulfuric acid. The product is collected by filtration.

(A=B=H, C=OOH$_3$, X=H)

EXAMPLE 27

Synthesis of 2-sulfo acridine-9-carboxylic acid

The title compound can be prepared from N-phenyl isatin 5 sulfonic acid of example 11 and 10% KOH by heating for hours on a steam bath. The solution is filtered, then acidified to pH 1 and product is collected by filtration.

(A=B=H, C=SO$_3$H, X=H)

EXAMPLE 28

Synthesis of 4 methyl acridine 9 carboxylic acid

The title compound can be prepared from N phenyl 7-methyl isatin of example 12 and 10% KOH by heating for hours on a steam bath. The solution is filtered, then acidified to pH 1 with concentrated sulfuric acid, and then product collected by filtration. (A=CH$_3$, B=C=X=H)

EXAMPLE 29

Synthesis of 3 methyl acridine 9-carboxylic acid

The title compound can be prepared from N-phenyl-6 methyl isatin of example 13 and 10% KOH by heating on a steam bath for 12 hours. The solution is filtered, then acidified to pH 1 with concentrated sulfuric acid, and the product is collected by filtration.

(A=C=D=H, B=CH$_3$, X=H),

EXAMPLE 30

Synthesis of 2-aminoethyl-acridine-9 carboxylic acid

The title compound can be prepared from N-phenyl-5-(2-amino-ethyl)isatin of example 14 and 10% KOH by heating for 12 hours on a steam bath. The solution is filtered, then acidified with concentrated sulfuric acid to pH 1, and the product is collected by filtration.

(A=B=D=X=H, C=CH$_2$CH$_2$NH$_2$),

EXAMPLE 31

Synthesis of 2-methoxy acridine 9 carboxylic acid

The title compound can be prepared from N (4-methoxy phenyl) isatin of example 15 and 10% KOH by heating for 12 hours on a steam bath. The product is isolated as in example 25.

EXAMPLE 32

Synthesis of 1(3)nitro acridine 9-carboxylic acid

The title compound can be prepared from N-(3 nitrophenyl) isatin of example 17 and 10% KOH by heating for 12 hours on a steam bath. The solution is filtered, then acidified to pH 1 with conc. sulfuric acid, and the mixture of products isolated by filtration.

(A=B=C=H, X=1 NO$_2$ or 3-NO$_2$)

EXAMPLE 33

Synthesis of 4 methyl-acridine-9-carboxylate

The title compound can be prepared from N-(o-tolyl)isatin of example 18 and 10% KOH by heating for 12 hours on a steam bath. The product is isolated as in example 26.

(A=B=C=H, X=4=CH$_3$)

I claim:

1. A process for N-arylation of isatins, comprising:
   (a) reacting a compound of formula I wherein A,B,C, and D are selected independently in each instance from hydrogen, halogen, cyano, nitro, amino, carboxy, sulfone, alkyl, and alkoxy, or B and C together can form a fused aromatic ring;

(b) with a compound of formula II:

$$\left(X-\underset{}{\underset{}{\bigcirc}}-\right)_3 Bi(Z)_2 \quad \text{II}$$

wherein Z is a halogen or a substituent of formula $$-O-\overset{O}{\underset{\|}{C}}-R^*$$

with the proviso that where Z is a halogen, a salt of the formula $$Y-O-\overset{O}{\underset{\|}{C}}-R^*$$

is added to the reaction of compounds I and II where Y is a group I or group II metal, and R* in each instance is selected from a group such that the conjugate acid $$H-O-\overset{O}{\underset{\|}{C}}-R^*$$

of the group of formula II has a pKa in water of less than 5.0 and is other than trifluoroacetic acid;

(c) in the presence of a copper catalyst; whereby an N-arylated isatin of formula III is produced;

[Structure III]

2. The process of claim 1 wherein R* is selected from hydrogen, alkyl, halo-substituted alkyl, or cyano-substituted alkyl.

3. The process of claim 2 wherein R* is methyl.

4. A process of claim 1 wherein the reaction mixture is heated to reflux temperature during the reaction.

5. A process of producing an intermediate of formula IV, comprising:

(a) reacting a compound of formula I;

(b) with a compound of formula II;

$$\left(X-\underset{}{\underset{}{\bigcirc}}-\right)_3 Bi(O-\overset{O}{\underset{\|}{C}}-R^*)_2 \quad \text{II}$$

(c) in the presence of a copper catalyst to produce an N-arylated isatin of formula III;

[Structure III]

(d) and treating the N-arylated isatin of formula III with a strong base and heat to produce a compound of formula IV:

[Structure IV]

wherein A, B, C, and D are selected independently in each instance from hydrogen, halogen, cyano, nitro, amino, carboxy, sulfone, alkyl, and alkoxy, or B and C together can form a fused aromatic ring; wherein X is selected from hydrogen, halogen, nitro, cyano, alkyl, and alkoxy; and R* is selected from a group such that the conjugate acid $$H-O-\overset{O}{\underset{\|}{C}}-R^*$$

of the group of formula II has a pKa in water of less than 5.0 and is other than trifluoroacetic acid.

6. The process of claim 5 wherein R* is selected from hydrogen, alkyl, halo-substituted alkyl, or cyano-substituted alkyl.

7. The process of claim 6 wherein R* is methyl.

8. The process of claim 5 wherein the compound of formula II is generated in situ by reacting a compound of the formula

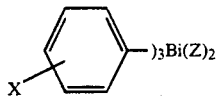
with a compound of the formula
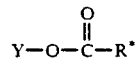
wherein X is selected from hydrogen, halogen, nitro, cyano, alkyl, and alkoxy; R* is selected from a group such that the conjugate acid
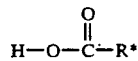
of the group of formula II has a pKa in water of less than 5.0 and is other than trifluoroacetic acid; and wherein Z is a halogen and Y is an alkali metal.
* * * * *